(12) United States Patent
Beretta

(10) Patent No.: US 6,565,580 B1
(45) Date of Patent: May 20, 2003

(54) MULTILAYER PROSTHESIS TO SURGICALLY CORRECT INGUINAL HERNIA

(75) Inventor: Luciano Beretta, Arcore (IT)

(73) Assignee: Sofradim Production, Trevoux (FR)

( * ) Notice: Subject to any disclaimer, the term of this patent is extended or adjusted under 35 U.S.C. 154(b) by 0 days.

(21) Appl. No.: 09/889,360
(22) PCT Filed: Jan. 19, 2000
(86) PCT No.: PCT/IT00/00014
§ 371 (c)(1), (2), (4) Date: Sep. 7, 2001
(87) PCT Pub. No.: WO00/42943
PCT Pub. Date: Jul. 27, 2000

(30) Foreign Application Priority Data

Jan. 19, 1999 (IT) .......................................... MI99U0028

(51) Int. Cl.[7] .............................................. A61B 17/08
(52) U.S. Cl. ........................ 606/151; 623/23.72; 600/37
(58) Field of Search .................... 623/11.11, 23.72, 623/23.74, 12, 66.1; 600/37; 606/151, 153, 157, 215, 216

(56) References Cited

U.S. PATENT DOCUMENTS

| 4,769,038 A | * | 9/1988 | Bendavid et al. ............ 606/151 |
| 4,854,316 A | | 8/1989 | Davis |
| 5,697,978 A | * | 12/1997 | Sgro ............................ 600/37 |
| 6,174,320 B1 | * | 1/2001 | Kugel et al. ................. 606/151 |
| 6,280,453 B1 | * | 8/2001 | Kugel et al. .................. 602/44 |

FOREIGN PATENT DOCUMENTS

| EP | 0 719 527 A1 | 7/1996 |
| WO | WO 96/14805 A1 | 5/1996 |

* cited by examiner

Primary Examiner—David J. Isabella
Assistant Examiner—Urmi Chattopadhyay
(74) Attorney, Agent, or Firm—Oliff & Berridge, PLC

(57) ABSTRACT

Inguinal hernia correcting prosthesis having an upper layer and a lower layer connected to each other by a flexible band, the flexible band having a first end fixed to the upper layer next to a recess provided on an edge of the upper layer, and a second end fixed next to a hole provided in the lower layer and connected by a cut to an external edge of the lower layer, the hole being axially aligned with the band and the recess.

4 Claims, 2 Drawing Sheets

MULTILAYER PROSTHESIS TO SURGICALLY CORRECT INGUINAL HERNIA

BACKGROUND OF THE INVENTION

1. Field of Invention

The present invention relates to a prosthesis to surgically correct inguinal hernia and particularly to a prosthesis formed of two parallel layers of biocompatible net which are joined one to the other in a translational way.

2. Description of Related Art

It is known that the wall defects of the inguinal canal, which cause inguinal hernia, are surgically corrected by means of prostheses formed of profiled pieces of biocompatible material, normally net-shaped. Said known prostheses are generally formed of a net sheet, provided with a hole for the passage of the spermatic cord, which is applied by the surgeon on the suprafascial plane parallel to the back wall of the inguinal canal (according to the well known Liechtenstein technique). This kind of prosthesis imply the risk of relapses especially in the region of the internal inguinal orifice, due to the fact that the prosthesis is applied on a plane which is considerably distant, above said orifice. Another kind of known prosthesis consists in a so-called "plug" of biocompatible material which is inserted like a stopper in the internal inguinal orifice. Inserting said kind of prosthesis implies drawbacks due to the patient's intolerance towards the material, because of the difficult incorporation of such a voluminous and tied up prosthesis.

Prostheses formed of many layers of biocompatible material have been recently proposed in the attempt to solve said drawbacks of the above described prostheses. EP-A-0719 527 describes a prosthesis for surgically correcting an inguinal hernia comprising an upper layer and a lower layer connected to each other by knitting. A hole is provided in said lower layer for the passage of the spermatic cord, and connected by means of a cut to an external edge of the same lower layer.

In WO96/14805 a prosthesis formed of two layers of biocompatible material which are applied one over the other on the same plane in the suprafascial region is described. Also this kind of prosthesis implies several drawbacks. The first drawback is that the plane of application of the prosthesis is above the fascia transversalis and therefore above the aponeurotic muscle, so that some of the drawbacks of the Liechtenstein method arise again. Further, this kind of prosthesis has another drawback, which is that the exit point of the cord from the prosthesis upper layer out of alignment with respect to the exit point of the cord of the underlying layer and therefore, since practically no space is provided between the two layers, the cord is pressed between the two layers of the prosthesis.

Further, a two layers prothesis has been recently marketed, which eliminates the first of the drawbacks of the prosthesis described in WO 96/14805 because one of the two layers is applied above the fascia transversalis and the other under said fascia, that is under the aponeurotic muscle plane. Consequently, the internal oblique and transverse muscles can keep exerting their "shutter" mechanism in a physiological way. However, even this recent kind of prosthesis is not free from drawbacks. For example, the central pin which connects the two layers represents an impediment for the above mentioned "shutter" mechanism. Further, said prosthesis does not provide for a suitable passage for the spermatic cord which, in order to come to the surface, is compelled to a route with a first curve and a second curve in the opposite direction and a consequent risk of "kneeling down" of the cord important structures.

BRIEF SUMMARY OF INVENTION

Object of the present invention is therefore providing a prosthesis which is free from the above described drawbacks and particularly a prosthesis with two layers which can be respectively applied above and under the fascia transversalis, in the meantime providing an anatomically physiological passage for the spermatic cord. Said object is obtained according to the present invention with the prosthesis having the features specified in claim 1. Further features of the prosthesis according to the present invention are specified in the dependent claims from 2 to 5.

The two layers prosthesis according to the present invention offers the advantage that the spermatic cord, besides finding a physiologically correct passage between the two layers of the prosthesis, does not present any risk of "kneeling down" or squashing.

Another advantage of the prosthesis according to the present invention is that the two layers, although they are suitably spaced from each other since they are applied respectively above and under the fascia transversalis, are joined together by a band which allows axial translations of the upper layer in order to enable a better adjustment to the unavoidable, although small, anatomic variables of the distance between the external edge of the lower portion of the cord and the tuberculum pubicum, that is the bone whereto the inguinal ligaments are fixed.

BRIEF DESCRIPTION OF DRAWINGS

These are other advantages of the prosthesis in two layers according to the present invention will appear to those which are skilled in the art from the following detailed description of an embodiment thereof with reference to the accompanying drawings, wherein.

DETAILED DESCRIPTION OF EMBODIMENTS

Figure 1:
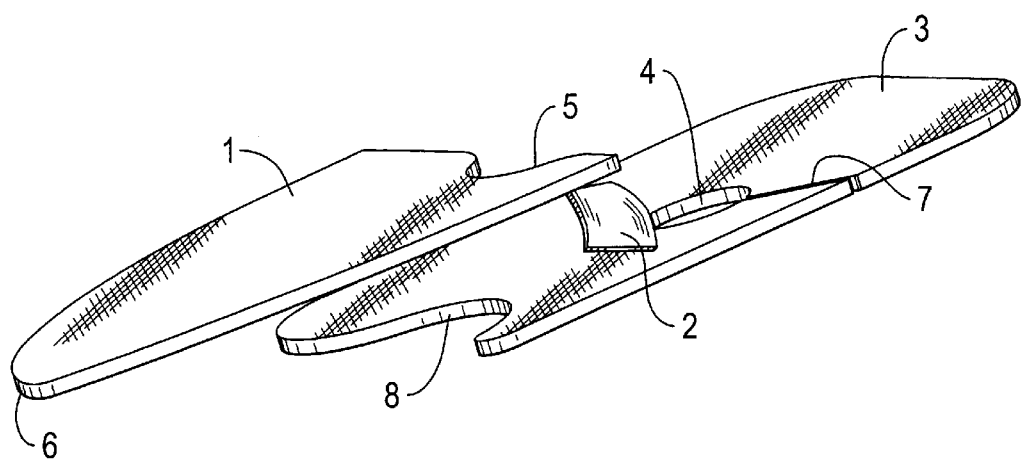
FIG. 1 shows a prospective view of an embodiment of the two layer prosthesis according to the present invention.

With reference to FIG. 1, the prosthesis according to the present invention is formed of an upper layer 1 connected to the lower layer 3 by means of flexible band 2. Upper layer 1 is intended to be applied above the back wall of the inguinal canal at the middle inguinal fossa. On the other side, lower layer 3 is intended to be applied under the back wall of the inguinal canal at the side inguinal fossa. The application of the two layers in the above described way ensures a certain correction of the wall defect at the level of the side inguinal fossa, since lower layer 3 strengthens or even substitutes the fascia transversalis while the upper layer 1 corrects the wall defects at the level of the middle inguinal fossa.

Lower layer 3 is suitably provided with hole 4 intended to create a suitable passage for the spermatic cord. Upper layer 1 is provided on the margin with a recess 5 which is also intended to leave a suitable passage for the spermatic cord when upper layer 1, after adjusting translations, rests against the spermatic cord. The final alignment of hole 4 and recess 5 ensures a substantially rectilinear route of the spermatic cord.

Band 2 is provided with one end fixed to layer 3 next to hole 4 and with the opposite end fastened to the upper layer 1, next to recess 5. Band 2 has the main function of keeping together the two layers and thus allowing the surgical application thereof. Band 2 is made with a flexible material so as to allow during the application thereof the axial translation movements of layer 1 with respect to layer 3. By virtue of the flexibility of band 2, recess 5 can be aligned with hole 4, thus allowing to the spermatic cord a substantially rectilinear passage as above said and according to the object of the present invention.

Figure 2:
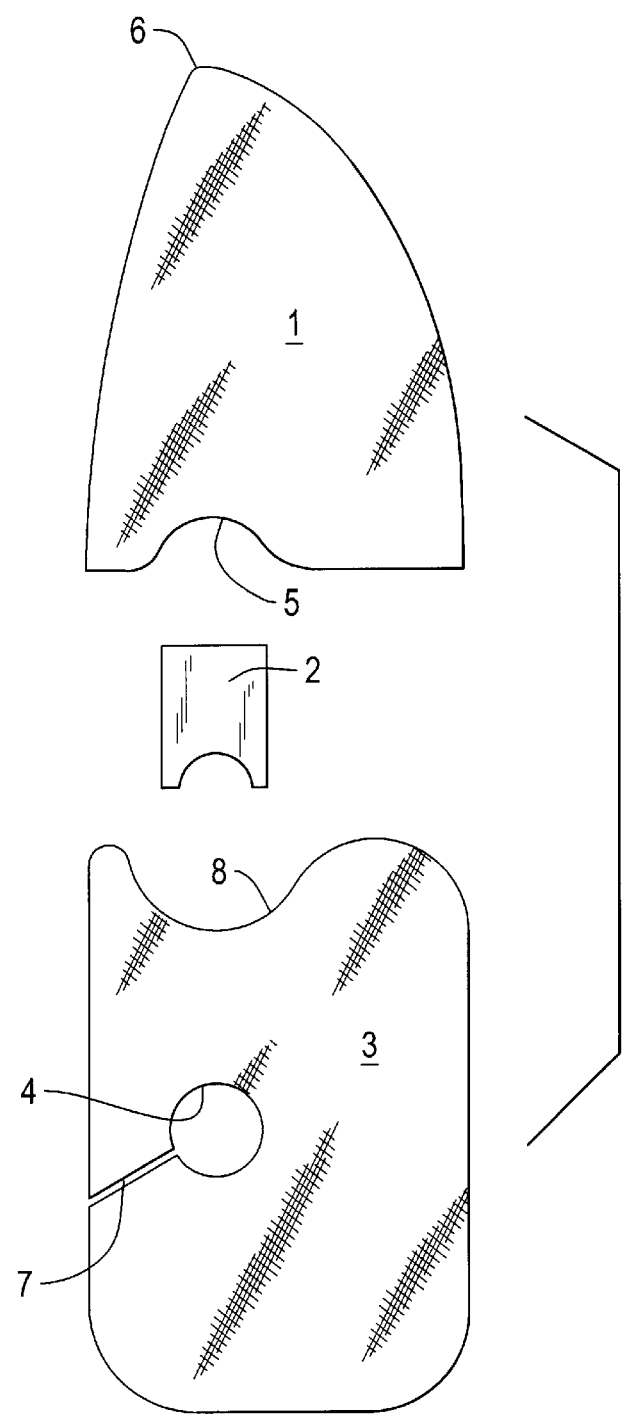
FIG. 2 shows a top plan view of the three portions which form the prosthesis of FIG. 1.

With reference to FIG. 2 it can be seen that the three components of the prosthesis according to the present invention are preferably profiled. Upper layer 1 is substantially shaped as a triangle having recess 5 at the base and the other two sides slightly arched so that the contour thereof is lance-shaped. Said contour enables inserting layer 1 in an anatomically more suitable way in an optimal position while the prosthesis is surgically applied. Point 6 of layer 1 is preferably out of alignment with respect to the base in order to follow the anatomical conformation of the inguinal ligament.

Band 2 is substantially tape-shaped and its width can be freely chosen, bearing in mind that it is preferable to make it as narrow as possible in line with the mechanical strength requested for holding together layers 1 and 3 of the prosthesis according to the present invention in a flexible although reliable way. The ends of the tape that forms band 2 are fixed to upper layer 1 next to recess 5 and to lower layer 3 next to hole 4.

Lower layer 3 is shaped as a rectangle having rounded corners. It is provided in the middle with hole 4 which is intended for the passage of the spermatic cord when the prosthesis is applied to the patient. In order to insert the cord into hole 4 during the surgical operation, lower layer 3 of the prosthesis according to the present invention is provided with a cut 7 connecting the side edge of layer 3 to hole 4. Thanks to said cut 7 the side of layer 3 can be slightly opened apart in order to let the spermatic cord pass until it reaches the inside of hole 4. Cut 7 is preferably made from the side edge of layer 3 nearest to hole 4. This allows to compromise as little as possible the stability and mechanical stiffness of layer 3, which has a great usefulness during the prosthesis application because it allows the surgeon to properly handle the prosthesis.

Lower layer 3 of the prosthesis according to the present invention is provided with a recess 8 made on the shorter side facing the base of layer 1. Said recess 8 has the function of allowing the surgeon to bring the adjacent rounded corners near to each other for inserting layer 3 in an easier way into the narrow passage under the epigastric vessels.

The sizes of the three components of the prosthesis according to the present invention can be freely chosen, since they are the result of a compromise between the requirements of the prosthesis surgical application and of its function once it is applied to the patient. Only as a non-limiting example of the present invention, it can be said that the base of layer 1 is about 5.4 cm long, the height thereof is 7.3 cm and the radius of curvature of the recess thereof is 0.8 cm. The shorter side of the lower layer 3 is 5.4 cm, the longer is 8.5 cm, the radius of curvature of recess 8 is 1.4 cm, the radius of hole 4 is 0.7 cm and the distance of the center of hole 4 from the longer side of layer 3 is 1 cm. The length of cut 7 is therefore about 0.8 cm, but it can be longer if it is oblique, which is also the preferred possibility.

The material for making the prosthesis according to the present invention can be any biocompatible material already used for the prostheses according to the state of the art. As shown in FIG. 2, the material used for lower layer 3 can be different from the one used for upper layer 1.

What is claimed is:

1. Inguinal hernia correcting prosthesis, comprising a first layer (1) and a second layer (3) connected to each other, said second layer having a hole (4) and a cut (7) connecting said hole to an external edge of said second layer, wherein said first layer (1) has a recess (5) provided on an edge of said first layer, and said prosthesis further comprises a connecting flexible band (2) which has a first end fixed to said first layer (1), next to said recess (5), and a second end fixed to said second layer (3) next to said hole (4), said recess (5) being arranged to be aligned with said hole (4) along a substantially rectilinear passage for the spermatic cord, by virtue of the flexibility of said band (2), wherein said prosthesis is shaped and configured to correct inguinal hernias.

2. Prosthesis according to claim 1, wherein said first layer (1) is shaped as a triangle having two longer sides and a base side, wherein the longer sides are slightly arched and a point (6) wherein the longer sides meet is substantially aligned with the recess (5), which is provided on said base.

3. Prosthesis according to claim 1, wherein said second layer (3) is shaped as a rectangle having a first shorter side farthest from said first layer (1), a second shorter side closest to said first layer (1), and rounded corners, and is provided with said hole (4) in the middle thereof.

4. Prosthesis according to claim 3, wherein said second layer (3) is provided with a recess (8) on said second shorter side.

* * * * *